United States Patent

Depernet et al.

Patent Number: 5,326,878
Date of Patent: Jul. 5, 1994

[54] METHOD FOR THE RESOLUTION OF CHIRAL HYDANTOINS

[75] Inventors: Dominique Depernet, Brissac-Quince; Roger Bouaziz, Paris; Gerard Coquerel, Notre Dame de Bondeville; Marie N. Petit, Mont-Saint-Aignan, all of France

[73] Assignee: Jouveinal SA, Paris, France

[21] Appl. No.: 910,184

[22] PCT Filed: Nov. 15, 1991

[86] PCT No.: PCT/FR91/00906
§ 371 Date: Jul. 21, 1992
§ 102(e) Date: Jul. 21, 1992

[87] PCT Pub. No.: WO92/08702
PCT Pub. Date: May 29, 1992

[30] Foreign Application Priority Data

Nov. 16, 1990 [FR] France ................. 90 14487

[51] Int. Cl.$^5$ ............ C07D 417/04; C07D 233/74
[52] U.S. Cl. ..................... 548/315.1; 548/317.1; 548/320.5; 548/321.1
[58] Field of Search ........... 548/315.1, 317.1, 320.5, 548/321.1

[56] References Cited

U.S. PATENT DOCUMENTS 4,634,713 1/1987 Werner et al. ............... 548/318 X

Primary Examiner—Mary C. Lee
Assistant Examiner—Jacqueline Haley
Attorney, Agent, or Firm—Pennie & Edmonds

[57] ABSTRACT

Method of resolution of chiral hydantoins of the general formula I

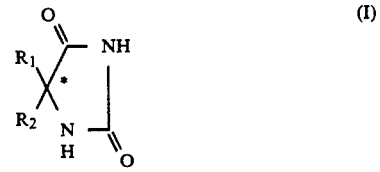

in which:
  $R_1$ designates a lower alkyl radical comprising 1 to 5 carbon atoms in linear or branched chain,
  $R_2$ designates a phenyl radical, possibly mono-, di-, or tri-substituted by lower alkyl or alkoxy radicals or halogen atoms, whether identical of different, or a heteroaryl radical containing a ring of 5 to 7 members in which the sole hetero atom is nitrogen, oxygen or sulfur, or else an aralkyl radical the alkyl part of which comprises one or two carbon atoms and the aryl ring is a phenyl group possibly mono-, di- or tri-substituted by radicals which are lower alkyl or alkoxy radicals or halogen atoms, whether identical or different. The hydantoin (I) to be resolved is dissolved in an alcohol or an alkaline solution, and an enantiomer of α-methylbenzylamine is added in a defined proportion to the solution obtained, whereupon the diastereoisomeric salt obtained is isolated and treated with an acid solution in order to crystallize the enantiomer of hydantoin (I).

14 Claims, No Drawings

METHOD FOR THE RESOLUTION OF CHIRAL HYDANTOINS

The present invention relates to a method for the resolution of chiral hydrantoins of general formula I:

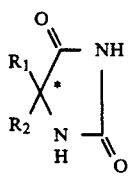

in which $R_1$ is a lower alkyl radical having 1 to 5 carbon atoms with linear or branched chain;

$R_2$ is a phenyl radical, possibly mono-, di- or tri-substituted by lower alkyl or alkoxy radicals or halogen atoms, which are identical or different, or a heteroaryl radical containing a ring of 5 to 7 members in which the only heteroatom is the nitrogen, oxygen or sulfur, or else an aralkyl radical, the alkyl part of which comprises one or two carbon atoms and the aryl cycle is a phenyl group, possibly mono, di- or tri-substituted by lower alkyl or alkoxy radicals or identical or different halogen atoms.

It is known that the resolution of chiral molecules conventionally makes use of the formation of diastereoisomeric salts the differences in solubility of which permit the separation of one or them, which is then decomposed to lead to the selected enantiomer.

It is also known that these methods use optically active resolution agents which are frequently toxic or unstable and which are offered on the market on an industrial scale in a form of very relative purity and/or costly form and that, furthermore, frequently only a single enantiomeric form of the resolution agent is proposed.

The importance of chiral hydantoin enantiomers is also known, particularly the enantiomers of hydantoins of formula I. Thus, the racemic hydantoin (I) in which $R_1$ is an ethyl radical and $R_2$ a phenyl radical has been used for its anti-convulsant properties in the treatment of epilepsy under the name "phenytoin" or else "Nirvanol" (DCI). Its analog, which is N-methylated in 3 position of the hydantoin ring, has the same properties and has been used under the name of "mephenytoin". Now, among other writers, Kuepfer et al (J. Pharmacol. Exp. Ther. 221 (3), 590–7, 1982 and 230 (1) 28–33, 1984) have noted in man, in the case o these two compounds, differences in bioavailability and metabolism which can be used for improving the treatment of convulsive attacks.

Furthermore, the chiral hydantoins (I), which are easily prepared from the corresponding $R_1$—CO—$R_2$ carbonyl derivatives by the Bucherer-Berg reaction, are intermediaries of choice for the preparation of acid amino enantiomers of general formula II:

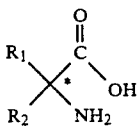

in which $R_1$ and $R_2$ have the meanings previously indicated for the hydantoins (I).

Some of these enantiomers exhibit interesting antihypertensive properties, such as, in particular, "methyldopa" (DCI) which is the levorotatory enantiomer of the amino acid in which $R_1$ is a methyl radical and $R_2$ a 3,4-dihydroxybenzyl radical. Other optically active amino acids are intermediates of choice for the preparation of therapeutically active compounds.

Thus the enantiomers and the racemic of the amino acid in which $R_1$ is a methyl radical and $R_2$ a 3,4-dichlorobenzyl radical lead, after reduction by metallic or organo metallic hydrides, to amino alcohols, some of which, N-substituted, described in Document FR-A-86 01 295, have analgesic properties and are active on the central nervous system.

The optically active amino acids in which $R_1$ is an ethyl radical and $R_2$ is a phenyl radical or a thienyl radical also permit, after their reduction in amino alcohols, the obtaining of amino esters or amino ethers which are active on the gastrointestinal tract, like some of the compounds described in FR-A-2 643 369 and EP-A-0 297 782.

In order to effect the resolution of the chiral hydantoins (I), various methods have been proposed. Thus, methods of preferred crystallization have been proposed which require a crystal seeding with an enantiomeric form previously obtained and which are generally of poor yield. Chromatographic techniques on chiral support have also been proposed, they being little adapted to industry and being particularly expensive. Finally, various methods have been proposed which are based on the formation of diastereoisomeric salts with enantiomers of different amines which are generally expensive while being of doubtful stability and industrial purity.

None of these methods is suitable for reliable and economic industrial application for the resolution of chiral hydantoins of formula I.

The present invention makes it possible to overcome these drawbacks by proposing a method of resolution which employs an optically active resolution agent of current use, namely α-methylbenzylamine, in the form of its (R)(+) and (S)(−) isomers, both of which are commercially available, and the physical-chemical properties of which (solubility, boiling point) permit recovery thereof and easy industrial recycling.

The method of the invention is characterized essentially by the fact that it consists in dissolving the chiral hydantoin (I) to be resolved in an alcohol or an alkaline solution, adding one of the enantiomers of α-methylbenzylamine in defined proportion to the solution obtained and then isolating the resultant diastereoisomeric salt and treating it with an acid solution in order to crystallize the enantiomer of the hydantoin (I) which is thus obtained under satisfactory conditions of yield and optical purity.

A first manner of carrying out the method of the invention consists in dissolving the chiral hydantoin (I) to be resolved in an alcohol and then adding the enantiomer of the α-methylbenzylamine in an amount of at least four molar equivalents to one mol of hydantoin to be resolved, so as to obtain the crystallization of the diastereoisomeric salt alone.

After filtration, this salt is treated with an excess of an acid solution in order to separate by crystallization the purified enantiomer of the hydantoin (I) from it, it being then filtered.

The isolated crystals show an optical purity which may reach 97%, disclosed by the analytical methods currently employed, namely determinations of the rotatory power and of the melting point, as well as high performance liquid chromatography (HPLC) on a column of a suitable chiral support, which analyses can be confirmed by other methods, such as radiocrystallography and infrared spectrography.

In this first embodiment of the method of the invention, the alcohol used comprises from one to three carbon atoms and has a boiling point equal to or less than 125.C under atmospheric pressure.

Among the alcohols suitable for use, methanol, ethanol and 2-methoxyethanol are particularly preferred.

The acid solution used to treat the diastereoisomeric salt is advantageously an aqueous solution of a strong inorganic acid, preferably a solution of hydrochloric acid, in particular a solution having a concentration of 1N to 5N.

A second embodiment of the method of the invention consists in dissolving the chiral hydantoin (I) to be resolved in an alkaline solution and then adding the enantiomer of the α-methylbenzylamine in an amount of at least one molar equivalent to one mol of hydantoin to be resolved, so as to obtain the crystallization of a diastereoisomeric salt, and then treating the latter by the method of operation previously described so as to obtain one of the enantiomers of the hydantoin (I).

In this second embodiment of the method of the invention, the alkaline solution may be:
- either an aqueous solution containing ammonia, an inorganic hydroxide or a water-soluble organic base;
- or an aqueous solution of an inorganic hydroxide associated with a cosolvent of a boiling point of less than 100° C., which may be a water-soluble alcohol comprising 1 to 3 carbon atoms or, preferably, acetone.

In the event that the alkaline solution is an ammoniacal aqueous solution, it is advisable to use at least three molar equivalents of ammonia in order to obtain suitable results both from the standpoint of optical purity and from the standpoint of weight yield.

In the event that the alkaline solution is an aqueous solution of an inorganic hydroxide, the latter is preferably a hydroxide of an alkaline metal and, more particularly, sodium hydroxide. In this case, for one molar equivalent of chiral hydantoin (I), the resolution is effected in the presence of about 0.5 molar equivalent of sodium hydroxide, adding one to three molar equivalents of the enantiomer of α-methylbenzylamine.

However, the preferred method used is that which employs an inorganic hydroxide and an enantiomer of α-methylbenzylamine in alkaline aqueous medium with which acetone is associated as preferred co-solvent in an amount of 0.2 to 10 parts per volume to one part by volume of aqueous solution, the mixture of one part by volume of water with 0.5 to 2 parts by volume of acetone generally leading to satisfactory results.

The following examples are given by way of illustration and not of limitation of the applications of the method forming the object of the invention.

EXAMPLE 1

Resolution in Alcoholic Medium of (+/−) 5-Phenyl-5-ethylhydantoin (Designated by the Abbreviation PEHYD in the Following)

About 2.04 g of (+/−) PEHYD (0.01 mol) and an amount of alcohol necessary for the dissolving of the product, such as indicated in the summary table which follows, are introduced into a 250 ml flat-bottom flask.

After dissolving in the hot, 4.84 g of (S)(−)α-methylbenzylamine (0.04 mol) are added. The diastereoisomeric salt which precipitates is filtered, washed with water, and then treated with an excess of a 1N solution of HCl in order to obtain the enantiomer of PEHYD.

The precipitation is completed with agitation at 10° C. for two hours. The insoluble matter is filtered off, washed with water, and dried to constant weight by desiccation under vacuum at 50° C.

The determination of the rotatory power of the product in solution in ethanol (c=2) shows that the product obtained is the levorotatory enantiomer of PEHYD.

The value of the rotatory power found under these conditions is compared with that determined by Sobotka et al. (J. Am. Chem. Soc., 1932, 54, 4697–702): $[\alpha]_D = +123°$ (c about 2% in EtOH) in order to determine in % the optical purity of the product obtained.

The tests and the results obtained are reported in the following table, in which the yield expressed in % corresponds to the product of the weight yield of the resolution in % multiplied by the optical purity in % of the enantiomer obtained.

| Example | Alcohol | Wgt. (g) of solvent | (−) PEHYD obtained (g) | Optical purity (%) | Yield (%) |
|---|---|---|---|---|---|
| 1-a | $CH_3OH$ | 4.4 | 0.54 | 88 | 47 |
| 1-b | $C_2H_5OH$ | 10 | 0.63 | 93 | 57 |
| 1-c | $C_2H_5OH$ | 9 | 0.65 | 74 | 47 |
| 1-d | 2MeOEtOH | 17.9 | 0.63 | 97 | 60 |

These tests, in particular in ethanol (example 1-b) and 2-methyoxyethanol (example 1-d) are probative, both from the point of view of the optical purity and of the yield, of the effectiveness of the method of the invention.

EXAMPLE 2

Resolution in Aqueous Ammoniacal Solution of the (+/−) PEHYD

Proceeding in accordance with the procedure of Example 1, starting from 0.01 mol of (+/−) PEHYD in ammoniacal solution, various resolution tests are carried out with 1.21 g (0.01 mol) of (R)(+)-α-methylbenzylamine.

The enantiomer obtained is the dextrorotary isomer (+) PEHYD.

The conditions of the tests and the results obtained are recapitulated in the following table.

| Example | V-water (ml) | Mols $NH_3$/ Mols (+/−) PEHYD | (+) PEHYD obt. (g) | Optical purity (%) | Yield (%) |
|---|---|---|---|---|---|
| 2-a | 70 | 3 | 0.81 | 73 | 58 |
| 2-b | 80 | 3 | 0.89 | 63 | 55 |
| 2-c | 90 | 3 | 0.85 | 71 | 60 |
| 2-d | 100 | 3 | 0.58 | 99 | 56 |

-continued

| Example | V-water (ml) | Mols NH₃/ Mols (+/−) PEHYD | (+) PEHYD obt. (g) | Optical purity (%) | Yield (%) |
|---|---|---|---|---|---|
| 2-e | 70 | 6 | 0.59 | 97 | 56 |

These tests are probative of the effectiveness of the resolution effected in ammoniacal solution, in particular tests 2-d and 2-e, which lead to the obtaining of a product of high optical purity.

EXAMPLE 3

Resolution of (+/−) PEHYD in Aqueous Sodium Hydroxide Solution

Proceeding in accordance with the procedure set forth in Example 1, starting with 0.01 mol of (+/−) PEHYD and 0.01 mol of (R)(+)α-methylbenzylamine, and varying the ratios of mols of NaOH to mols of (+/−) PEHYD, the tests of Examples 3-a to 3-i are carried out, the conditions and results of which are indicated in the following table, the isolated enantiomer being the (+) PEHYD.

| Example | V-water (ml) | Mols NaOH/ Mols (=/−) PEHYD | (+) PEHYD obtained (g) | Optical purity (%) | Yield (%) |
|---|---|---|---|---|---|
| 3-a | 110 | 0.125 | 1.21 | 23 | 27 |
| 3-b | 110 | 0.166 | 1.15 | 25 | 28 |
| 3-c | 110 | 0.250 | 1.06 | 40 | 42 |
| 3-d | 110 | 0.33 | 0.96 | 58 | 54 |
| 3-e | 110 | 0.40 | 0.85 | 71 | 61 |
| 3-f | 110 | 0.45 | 0.74 | 91 | 65 |
| 3-g | 110 | 0.50 | 0.63 | 96 | 60 |
| 3-h | 110 | 0.60 | 0.45 | 97 | 43 |
| 3-i | 110 | 0.75 | 0.38 | 98 | 37 |

The tests of examples 3-g to 3-i in which the sodium hydroxide is used in an amount of 0.50 to 0.75 equivalents referred to the (+/−) PEHYD, make it possible to obtain the enantiomer (+) with satisfactory optical purity but to the detriment of the yield with the larger quantities of sodium hydroxide (example 3-i).

EXAMPLE 4

In accordance with the manner of procedure of example 3-g above, examples 4-a and 4-b are carried out by modifying the amount of (R)(+)-α-methylbenzylamine used. The results of these tests compared to that of example 3-g are indicated in the following table.

| Example | Mols NaOH/ Mols PEHYD | Mols (R/+) amine/ Mols (+/−) PEHYD | (+) PEHYD obtained (g) | Optical purity (%) | Yield (%) |
|---|---|---|---|---|---|
| 4-a | 0.50 | 0.5 | 0.79 | 30 | 23 |
| 3-g | 0.50 | 1.0 | 0.63 | 96 | 60 |
| 4-b | 0.50 | 2.0 | 0.67 | 99 | 66 |

The tests of examples 3 and 4 show that the best results are obtained when using, for the resolution of one mol of (+/−) PEHYD, 2 molar equivalents of o-methylbenzylamine and 0.5 · molar equivalents of NaOH, excellent results being still obtained with one molar equivalent of α-methylbenzylamine and 0.45 to 0.5 molar equivalent of NaOH.

EXAMPLE 5

In accordance with the procedure of Example 3, the method of resolution in aqueous sodium hydroxide solution is applied to various chiral hydantoins (I).

Each resolution is effected on basis of 0.01 mol of chiral hydantoin (I) with (R)(+)α-methylbenzylamine.

The hydantoin enantiomers obtained after resolution result in a dextrorotatory deviation in solution in ethanol.

The products subjected to the resolution, the conditions of the tests and the results obtained are set forth in the following table.

TESTS OF EXAMPLE 5

| Example | R₁ | R₂ | Water V (ml) (1) | NaOH mMols (1) | (R/+)-amine mmols (1) | Optical purity (%) (2) | Yield (%) (3) | $[\alpha]_D$ (4) | MP |
|---|---|---|---|---|---|---|---|---|---|
| 5-a | methyl | phenyl | 59.0 | 3.8 | 10 | 97 | 62 | +116° | 242° C. |
| 5-b | methyl | p-tolyl | 27.5 | 7.5 | 15 | 99 | 35 | +105° | 249° C. |
| 5-c | n-propyl | phenyl | 27.0 | 7.0 | 30 | 91 | 30 | +107° | 162° C. |
| 5-d | i-propyl | phenyl | 27.0 | 7.0 | 30 | 67 | 30 | +150° | 213° C. |
| 5-f | methyl | phenethyl | 27.5 | 7.5 | 30 | 74 | 16 | +17° | 184° C. |

(1) for 10 mmols of chiral hydantoin (I)
(2) determined by HPLC
(3) Yield % weight yield × optical yield/100
(4) (c = 1; EtOH)

EXAMPLE 6

Resolution of (+/−)PEHYD in Aqueous Sodium Hydroxide Solution, With Acetone as Co-solvent In a reactor equipped in reflux position, 20.0 g (0.098 mol) of (+/−)PEHYD are dissolved in 200 ml of an acetone/water mixture (V/V). 1.76 g (0.044 mol) of sodium hydroxide in pellets is added, and then 12.2 g (0.098 mol) of (S)(−)α-methylbenzylamine is added.

The suspension is agitated while gradually heating in order to obtain at 65° C. the complete dissolving of the reagents, whereupon the solution is cooled slowly to a temperature of about 40° C., at which crystallization commences. After being kept at this temperature for one hour in order to favor the crystalline development, the medium is cooled gradually to 20°–25° C. and then set aside overnight with agitation.

The insoluble matter is filtered, washed with 100 ml of water and, with agitation and without exceeding 20° C., the suspension is acidified to a pH of 1 by the addition of 4.0 ml of concentrated hydrochloric acid, causing the precipitation of the levorotatory enantiomer of the PEHYD, which is filtered, washed with water, and then dried under vacuum at 50° C.

There are obtained 5.4 g of (S)(−) PEHYD of a melting point of 241.4° C. and an optical purity (HPLC) of 100%, the yield of the operation being 54%.

EXAMPLE 7

Resolution of (+/−)5-Thienyl)-5-ethyl Hydantoin ($R_1$=Ethyl, $R_2$=2-Thienyl) in Aqueous Sodium Hydroxide Solution 10.5 g (0.05 mol) of (+/−)5-(2-thienyl)-5-ethyl hydantoin is added to 550 ml of demineralized water in a one liter reactor. 2.5 ml of 10 N solution of sodium hydroxide (0.025 mol) is added with agitation. After 10 minutes, a solution is obtained to which 6.1 g (0.05 mol) of (L)(−)-α-methylbenzylamine is added drop by drop at 25°–30°.

By maintaining under agitation and gradually cooling to 10° C., crystallization slowly appears.

After agitation overnight at this temperature, the crystalline distereoisomeric salt is filtered and suspended with agitation in a 1 N hydrochloric acid solution for 15 minutes.

The enantiomer obtained is (L)(−)5-(2-thienyl)-5-ethyl hydantoin, which is filtered, washed with water, and dried under vacuum at 50° C.

Weight obtained=1.35 g
Chemical yield=26%
$[\alpha]_D$=−135° (c=1, EtOH)
Optical purity=99% (HPLC)
Yield=25%

EXAMPLE 8

Resolution of (+/−)5-(3,4-Dichlorobenzyl)-5-Methyl Hydantoin ($R_1$=Methyl, $R_2$=3,4-Dichlorobenzyl) in Aqueous Solution of an Inorganic Hydroxide Associated With Acetone a) Preparation of the racemic hydantoin 160.0 g (0.79 mol) of 3,4-dichlorophenylacetone in 700 ml of ethanol is introduced in a reactor and the mixture is heated to 40° C. in order to effect the dissolving. 53.0 g (0.81 mol) of potassium cyanide, 149.0 g of ammonium sesquicarbonate, and 700 ml of water are then added.

The mixture is heated with agitation at a temperature of between 65° and 70° C. for 15 hours. The suspension is cooled with agitation to 10°–15° C. and set aside for 16 hours at this temperature. The insoluble matter is filtered, washed with water, and then with di-isopropyl ether before being dried under vacuum at 50° C. to constant weight.

155.0 g of product of a melting point of 240° C. are obtained; the yield of the operation is 72%.

b) Resolution of the racemic hydantoin 100 ml of demineralized water is mixed with 150 ml of acetone in a reactor equipped in reflux position, whereupon 3.7 g (0.091 mol) of sodium hydroxide in pellet form are added.

50.0 g (0.183 mol) of (+/−)5-(3,4-dichlorobenzyl)-5methyl hydantoin and 22.2 g (0.183 mol) of (R)(+)α-methylbenzylamine are then added in succession.

The mixture is brought to reflux with agitation until the reagents are dissolved. 100 ml of water is then added, heating the mixture gradually to 70° C., whereupon the solution is cooled slowly with agitation.

Crystallization commences at about 60° C. and the mixture is then maintained for one and a half hours at 50° C. in order to complete the crystallization, whereupon it is cooled to about 20° C. for 30 minutes.

The crystalline precipitate is filtered and then washed twice with 100 ml of a 2:1 acetone/water mixture (vol/vol).

The insoluble matter is suspended, as is, in 250 ml of water and the mixture is acidified to a pH of 1 by gradual addition of a concentrated hydrochloric acid solution.

The insoluble matter is filtered off and washed with water. The optical purity of the product determined by HPLC on an aliquot portion is 98.6%.

The wet product is recrystallized under reflux in 200 ml of a 1:1 water/acetone mixture (vol/vol).

After cooling for two hours at 15° C., the insoluble matter is filtered off, washed with an acetone/water mixture and then dried under vacuum at 50° C.

18.79 g of the (−)enantiomer of 5-(3,4-dichlorobenzyl)-5-methyl hydantoin are obtained.

Yield=75%
Optical purity=100% (HPLC)
Mp=276° C. $[\alpha]_D$=−28.4° (c=1, EtOH)

This method of resolution, effected with the (S)(−)α-methylbenzylamine leads to the (+)enantiomer of the 5-(3,4-dichlorobenzyl)-5-methyl hydantoin.

Yield=52%
Optical purity=100 % (HPLC)
MP>260° C.
$[\alpha]_D$=+26.5° (c=1, EtOH)

We claim:

1. A method of resolving a chiral hydrantoin of the formula

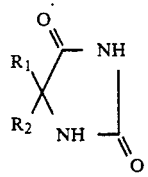

in which $R_1$ is lower alkyl and $R_2$ is phenyl, phenyl-$C_{1-2}$-alkyl or a 5 to 7 membered heterocyclic ring in which one ring member is nitrogen, oxygen or sulfur, wherein any phenyl group is optionally substituted 1 to 3 times by the same or a different lower alkyl or alkoxy group or halogen, the method comprising
 dissolving the chiral hydantoin to be resolved in an alkaline solution, combining the alkaline solution with at least one molar equivalent of an enantiomer of α-methylbenzylamine per mole of hydantoin to be resolved, recovering the resulting diastereoisomeric salt and contacting the diastereoisomeric salt with an acid solution to crystallize the enantiomer of the hydantoin.

2. The method of claim 1 wherein the alkaline solution is an aqueous solution containing at least 3 ammonia equivalents per mole of hydantoin to be resolved.

3. The method of claim 1 wherein the alkaline solution is an aqueous solution containing 0.3 to 0.75 equivalent of alkaline hydroxide per mole of hydantoin to be resolved.

4. The method of claim 3 in which the hydroxide is sodium hydroxide.

5. The method of claim 3 in which the aqueous alkaline hydroxide solution contains a co-solvent selected from the group consisting of water soluable alcohol and acetone.

6. The method of claim 5 in which the co-solvent is acetone in an amount of 0.2 to 10 parts by volume per part by volume of aqueous solution.

7. The method of claim 1 wherein the hydrantoin to be resolved is (+/−)-5-phenyl-5-ethyl-hydrantoin.

8. The method of claim 1 wherein the hydrantoin to be resolved is (+/−)-5-p-tolyl-5-methyl hydrantoin.

9. The method of claim 1 wherein the hydrantoin to be resolved is (+/−)-5-phenyl-5-n-propyl hydrantoin.

10. The method of claim 1 wherein the hydrantoin to be resolved is (+/−)-5-phenyl-5-i-propyl hydrantoin.

11. The method of claim 1 wherein the hydrantoin to be resolved is (+/−)-5-(2-thienyl)-5-ethyl hydrantoin.

12. The method of claim 1 wherein the hydrantoin to be resolved is (+/−)-5-(3,4-dichlorobenzyl)-5-methyl-hydrantoin.

13. The method of claim 1 wherein the hydrantoin to be resolved is (+/−)-5-phenethyl-5-methyl-hydrantoin.

14. The method of claim 1 in which the lower alkyl and alkoxy groups contain 1 to 5 carbon atoms and the heterocyclic ring is thienyl.

* * * * *